United States Patent [19]

Fancher

[11] 4,000,253
[45] Dec. 28, 1976

[54] CARBAMYLOXY PHENYL ISOTHIOCYANATES

[75] Inventor: Llewellyn W. Fancher, Orinda, Calif.

[73] Assignee: Stauffer Chemical Company, Westport, Conn.

[22] Filed: Mar. 12, 1975

[21] Appl. No.: 557,544

[52] U.S. Cl. .............................. 424/300; 260/454; 71/67

[51] Int. Cl.$^2$ ................. A01N 9/12; C07C 161/04

[58] Field of Search ................... 260/454; 424/300

[56] References Cited

FOREIGN PATENTS OR APPLICATIONS 1,481,055  12/1965  France ........................... 260/454

Primary Examiner—Lewis Gotts
Assistant Examiner—D. R. Phillips
Attorney, Agent, or Firm—Joel G. Ackerman

[57] ABSTRACT

New compounds having the formula:

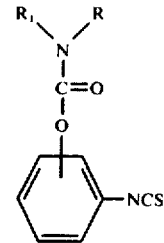

in which R is hydrogen or methyl and $R_1$ can be selected from the group consisting of lower alkyl, alkenyl, cyclohexyl, phenyl and substituted phenyl in which the substituents can be selected from the group consisting of halo, lower alkoxy, nitro, lower alkyl and thio-lower alkyl. The compounds are useful as fungicides, bactericides and algaecides.

26 Claims, No Drawings

CARBAMYLOXY PHENYL ISOTHIOCYANATES

The compounds of the present invention are carbamyloxy phenyl isothiocyanates represented by the general formula:

![formula showing R1, R on N, bonded to C=O, bonded to O, bonded to phenyl ring with NCS substituent]

in which R is hydrogen or methyl and $R_1$ can be selected from the group consisting of lower alkyl, alkenyl, cyclohexyl, phenyl and substituted phenyl, in which the substituents can be selected from the group consisting of halo, lower alkoxy, nitro, alkyl and thio-lower alkyl. By "lower alkyl", "lower alkoxy" and "thio-lower alkyl" are meant those members containing from 1 to about 6 carbon atoms inclusive, preferably 1 to about 4 carbon atoms. The carbon atoms may be arranged in either straight chain or branched chain configurations. For example, the lower alkyl group may be methyl, ethyl, n-propyl, isopropyl, n-butyl, secbutyl, amyl, isoamyl, n-hexyl, isohexyl and the like; the lower alkoxy group may be methoxy, ethoxy, propoxy, butoxy, secbutoxy, and the like; the thio-lower alkyl group may similarly be thiomethyl, thioethyl, thiopropyl, thiobutyl and the like.

The isothiocyanate group and the carbamyloxy ($COONRR_1$) group may be disposed in either the para- or meta-position with respect to each other.

The compounds herein described can be prepared as follows:

A. When R is hydrogen, by the reaction of the corresponding isocyanate with either the para- or meta-isomer of hydroxyphenylisothiocyanate, according to the equation:

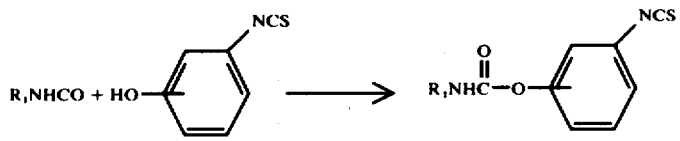

B. When R is methyl, by the reaction of the corresponding carbamyl halide with either the para- or meta-isomer of hydroxyphenylisothiocyanate, according to the equation:

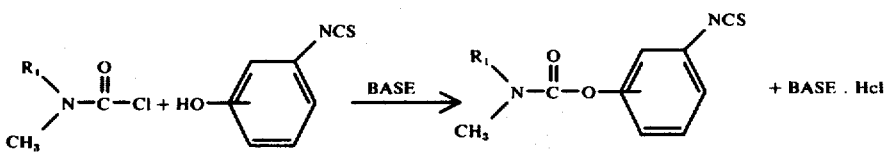

Table I lists representative compounds prepared according to the procedures described herein.

TABLE I

| COMPOUND NUMBER | R | $R_1$ | POSITION | MELTING POINT, °C. |
|---|---|---|---|---|
| 1 | H | $CH_3$ | para | 125–129 |
| 2 | H | phenyl | para | 139–142 |
| 3 | H | $CH_2-CH=CH_2$ | para | (waxy solid) |
| 4 | H | p-chlorophenyl | para | 128–131 |
| 5 | H | o-chlorophenyl | para | 108–110 |
| 6 | H | m-chlorophenyl | para | 103–108 |
| 7 | H | 3,4-dichlorophenyl | para | 119–124 |
| 8 | H | p-tolyl | para | 140–145 |
| 9 | H | p-methoxyphenyl | para | 140–146 |
| 10 | H | p-nitrophenyl | para | 172–175 |
| 11 | H | 3,4-xylyl | para | 117–121 |
| 12 | H | p-(thiomethyl)phenyl | para | 163–167 |
| 13 | H | cyclohexyl | para | 170–173 |
| 14 | H | $n-C_4H_9$ | para | 99–102 |
| 15 | H | p-ethoxyphenyl | para | 155–157 |
| 16 | H | $C_6H_5$ | para | 142–145 |
| 17 | H | $CH_3$ | meta | 74–76 |
| 18 | H | 3,4-dichlorophenyl | meta | 118–123 |
| 19 | $CH_3$ | $CH_3$ | para | * |

*Liquid, $n_D^{26}$ 1.5960

The following are specific illustrative examples of preparation of compounds of the present invention:

I. p-n-Butylcarbamyloxyphenylisothiocyanate (Compound No. 14)

Three and eight-tenths grams (3.8 g.) (0.025 m.) of p-hydroxyphenylisothiocyanate was mixed with 2.5 g. (0.025 m.) of n-butylisocyanate in 50 mls. of benzene. To this mixture was added 3 drops each of triethylamine and dibutyltin dilaurate, and the mixture was allowed to stand at ambient temperature over night. After refluxing on the steam-bath for thirty minutes, the solvent was removed under vacuum by means of a rotary evaporator. The residue was slurried in n-hexane, filtered and air dried. There was obtained 5.4 grams of solid, m.p. 99°–102° C. The structure was confirmed by I.R.

II.
3-(3',4'dichlorophenylcarbamyloxy-phenylisothiocyanate(Compound No. 18)

Three grams (3.0 g.) (0.02 m.) of m-hydroxyphenylisothiocyanate was mixed with 3.8 g. (0.02 m.) of 3,4-dichlorophenylisocyanate, 25 mls. of acetone and 3 drops each of triethylamine and dibutyltin dilaurate. The mixture was then refluxed on the steam-bath for 1.5 hours. After removal of the solvent under vacuum and slurrying the residue in n-hexane, filtering and drying, there was obtained 6.4 g. of product, m.p. 118°–123° C. Structure was confirmed by I.R.

III. 4-N,N-Dimethylcarbamyloxy-phenylisothiocyanate (Compound No. 19)

Three grams (3.0 g.) (0.02 m.) of p-hydroxyphenylisothiocyanate was mixed with 25 mls. of benzene and 2.2 g. (0.02 m.) of N,N-dimethylcarbamylchloride. To this mixture was added 2.1 grams (0.02 m.) (2 mls.) of triethylamine and 0.5 g. of potassium iodide as a catalyst, and the mixture was refluxed for 3 hours. After several days, an additional 75 mls. of benzene was added to the mixture and it was washed with water, dried over anhydrous magnesium sulfate, filtered and solvent removed under vacuum. By this means, there was obtained 3.5 g. of liquid product, $n_D^{30}$ 1.5960. Structure was confirmed by I.R. and N.M.R.

IV. p-Phenylcarbamyloxyphenylisothiocyanate (Compound No. 2)

By a procedure similar to that of Example I, the above compound (5.2 g., m.p. 139°–142° C.) was prepared from 7.6 g. (0.05 m.) of p-hydroxyphenylisothiocyanate and 6.0 g. (0.05 m.) of phenyl isocyanate, using 35 mls. of benzene as a solvent and 2 drops each of triethylamine and dibutyltin dilaurate as catalysts.

V. p-Cyclohexylcarbamyloxyphenylisothiocyanate (Compound No. 13)

By a procedure similar to that of Example I, the above compound (3.9 g., m.p. 170°–173° C.) was prepared from 3.8 g. (0.025 m.) of p-hydroxyphenylisothiocyanate and 3.2 g. (0.025 m.) of cyclohexylisocyanate, using 50 mls. of benzene as a solvent and 3 drops each of triethylamine and dibutyltin dilaurate as catalysts.

VI. p-Allylcarbamyloxyphenylisothiocyanate (Compound No.3)

By a procedure similar to that of Example I, the above compound (11.1 g.) in the form of a waxy solid, was prepared from 9.1 g. (0.06 m.) of p-hydroxyphenylisothiocyanate and 5.0 g. (0.06 m.) of allylisocyanate, using 35 mls. of chloroform as a solvent and 3 drops each of triethylamine and dibutyltin dilaurate as catalysts.

In addition to the solvents given in the Examples, other suitable non-reactive solvents such as ethyl acetate, dioxane and the like, can be utilized.

As previously mentioned, the herein described compounds are biocidal agents, particularly useful as microbiostatic agents, and especially in controlling fungi. Some of the compounds in this group, particularly the compounds in which $R_1$ is n-butyl or is a halo substituted phenyl group, more particularly a phenyl having 1 or more chlorine atoms as constituents, (i.e.,

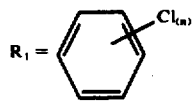

wherein $n$ is an integer from 1 to 2), are additionally useful as bactericides, and specifically in controlling the growth of *Staphylococcus aureus*, as will be seen from the experimental results which follow. At least one of the compounds has also been found to have algaecidal effect.

Tests of the compounds of this invention were conducted in the following manner.

In Vitro Vial Tests

Tubes of sterilized nutrient and malt extract broth are prepared. Aliquots of the toxicant, dissolved in an appropriate solvent, are injected through the stopper, into the broth, to provide concentrations ranging from 50 p.p.m. downward. The test organisms consist of two fungi, *Aspergillus niger* (A.n.) van Tieghem and *Penicillium italicum* (P.i.) Wehmer, and two bacteria, *Escherichia coli* (E.c.) Migula and *Staphylococcus aureus* (S.a.) Roseenbach. Three drops of a spore suspension of each of the fungi are injected into the tubes of malt broth and three drops of the bacteria are injected into the nutrient broth. One week later the growth of each organism is observed and effectiveness of the chemical is recorded as the lowest concentration in ppm which provides 50% inhibition of growth as compared to untreated inoculated tubes. The results of these tests are tabulated in Table II.

TABLE II

| Compound Number | A.n. | P.i. | E.c. | S.a. |
|---|---|---|---|---|
| 1 | 5 | 10 | >50 | >50 |
| 2 | 50 | >50 | >50 | >50 |
| 3 | 10 | 25 | >50 | >50 |
| 4 | >50 | >50 | >50 | 5 |
| 5 | 5 | 25 | >50 | 50 |
| 6 | 50 | >50 | >50 | 5 |
| 7 | >50 | >50 | >50 | 0.06 |
| 8 | >50 | >50 | >50 | >50 |
| 9 | >50 | >50 | >50 | >50 |
| 10 | 50 | 50 | >50 | >50 |
| 11 | >50 | >50 | >50 | >50 |
| 12 | 50 | >50 | >50 | >50 |
| 13 | >50 | >50 | >50 | >50 |
| 14 | 5 | 25 | >50 | 50 |
| 15 | >50 | 50 | >50 | >50 |
| 16 | 5 | 10 | >50 | >50 |
| 17 | 5 | 10 | >50 | >50 |
| 18 | 50 | 50 | >50 | 0.13 |
| 19 | 5 | 10 | >50 | >50 |

Compound 18 was subjected to additional tests as follows:

In Vitro Agar Screening Tests

This test measures the bactericidal, fungicidal and algaecidal properties of a compound when in contact with growing bacteria, fungi or algae in an artificial medium. The test is conducted by adding 20 ml. portions of a suitable warm sterile agar solution into 20 × 100 mm. Petri dishes. Then, the test compound, in 0.5% acetone solution, is added to the Petri dishes at levels of 1, 10 and 50 μg./ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30° C. and the bacteria are incubated at 37° C. The algae are incubated at room temperature under artificial light. Nutrient agar is used as the medium in this test for the bacteria. Potato dextrose agar is used as the medium for the fungi with the exception of *Pullularia pullulans* and *Trichophyton mentagro-*

*phytes* for which Emmons agar is used. A modified Jack Meyers agar is used for the growth of the algae.

The extent of growth is noted at the end of the incubation period.

Representative organisms used in this test are as follows:

Bacteria:
 Enterobacter aerogenes
 Bacillus cereus
 Pseudomonas aeruginosa
 Pseudomonas fluorescens
 Brevibacterium ammoniagenes
 Staphylococcus aureus
 Escherichia coli
Fungi:
 Aspergillus flavus
 Aspergillus fumigatus
 Aspergillus niger
 Aspergillus oryzae
 Penicillium italicum
 Penicillium expansum
 Penicillium sp.
 Rhizopus stolonifer
 Trichophyton mentagrophytes
 Pullularia pullulans
Algae:
 Scenedesmus obliquus
 Chlorella pyrenoidosa

TABLE III

| Bacteria | Minimum Inhibitory Concentration, µg/ml |
|---|---|
| Bacillus cereus | ( 1) |
| Brevibacterium ammoniagenes | 5 |
| Enterobacter aerogenes | (50) |
| Escherichia coli | >50 |
| Pseudomonas aeruginosa | >50 |
| Pseudomonas fluorescens | >50 |
| Staphylococcus aureus | 0.78 |
| Fungi | |
| Aureobasidium pullulans | (50) |
| Aspergillus flavus | >50 |
| Aspergillus fumigatus | (50) |
| Aspergillus niger | (10) |
| Aspergillus oryzae | 50 |
| Penicillium expansum | (10) |
| Penicillium ochra-chloron | (10) |
| Penicillium vermiculatum | 10 |
| Penicillium italicum | (10) |
| Phoma herbarum | (10) |
| Trichophyton mentagrophytes | (10) |
| Trichoderma sp. | 50 |
| Rhizopus stolonifer | 50 |
| Algae | |
| Chlorella pyrenoidosa | 5 |
| Euglena gracilis | — |
| Scenedesmus obliquus | 5 |

( ) = Partial control, complete control at next higher dosage

Sulfate Reducing Bacteria In Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 µg./ml. of solution. An inoculant solution of 0.5 ml. of the growing organism, *Desulfovibrio desulfuricans*, is added to the vials followed by sufficient sterile distilled water to give a total of 10 ml. of solution in the vials. The vials are incubated at room temprature for 3 to 5 days until untreated controls show growth of the organism as indicated by the black color development in the vials. The minimum inhibitory concentration of compound 18 necessary to control the organism was found to be 5 µg./ml.

Fungicide Testing Procedures

A. Foliar Preventative Sprays

1. Bean Rust. — The chemicals are dissolved in an appropriate solvent and diluted with water containing several drops of Tween 20, a wetting agent. Test concentrations, ranging from 1000 ppm downward, are sprayed to runoff on the primary leaves of pinto beans (*Phaseolus vulgarisl.*). After the leaves are dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm, which will provide 50% reduction in pustule formation as compared to untreated, inoculated plants.

2. Bean Powdery Mildew. — Test chemicals are prepared and applied in the same manner as for the bean rust test. After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in ppm, which will provide 50% reduction in pustule formation as compared to untreated, inoculated plants.

3. Tomato Early Blight. — Test chemicals are prepared and applied in the same manner as the bean rust and powdery mildew tests except that 4-week old tomato (*Lycopersicon esculentum*) plants are utilized as the host plant. When the leaves are dry, they are incoluated with a water suspension of spores of the early blight fungus (*Alternaris solani* Ellis and Martin) and placed in an environment of 100% humidity for 48 hours. The plants are then removed from the humidity chamber and held until disease lesions appear on the leaves. Effectiveness is recorded as the lowest concentration, in ppm, which will provide 50% reduction in number of lesions formed as compared to untreated, inoculated plants.

B. Tube Systemic Test

Bean Rust. — The chemicals are dissolved in an appropriate solvent and diluted with tap water to a series of descending concentrations beginning at 50 ppm. Sixty ml. of each concentration are placed in a test tube. A pinto bean plant is placed in each tube and supported with a piece of cotton so that only the roots and lower stem are in contact with the test solution. Forty-eight hours later the bean leaves are inoculated with a water suspension of spores of the bean rust fungus and placed in an environment with 100% humidity for 24 hours. The plants are then removed from the humidity chamber and maintained in the greenhouse until the disease pustules appear on the leaves. Effectiveness is recorded as the lowest concentration, in ppm, which will provide 50% reduction in pustule formation as compared to untreated, inoculated plants.

The results of these tests are tabulated in Table IV.

TABLE IV

| Compound Number | Foliar spray | | | Tube systemic |
| --- | --- | --- | --- | --- |
| | Rust | Mildew | Tomato blight | Rust |
| 1 | 1000 | >1000 | — | >25 |
| 2 | 1000 | >1000 | 1000 | >25 |
| 3 | 500 | 1000 | — | 25 |
| 4 | 1000 | >1000 | — | >50 |
| 5 | 1000 | >1000 | — | >50 |
| 6 | 1000 | >1000 | — | >50 |
| 7 | 1000 | >1000 | — | — |
| 8 | 500 | >1000 | >1000 | >50 |
| 9 | 500 | >1000 | — | >50 |
| 10 | 500 | >1000 | — | >50 |
| 11 | 500 | >1000 | — | >50 |
| 12 | 1000 | >1000 | — | >50 |
| 13 | 100 | >1000 | >1000 | >50 |
| 14 | 100 | >1000 | 500 | >50 |
| 15 | 100 | >1000 | >1000 | >50 |
| 16 | 100 | 500 | 1000 | >50 |
| 17 | 1000 | >1000 | — | — |
| 18 | 1000 | >1000 | — | >50 |
| 19 | >1000 | >1000 | — | — |

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.01 to 20% by weight of the active pesticide compound.

What is claimed is:

1. A compound having the formula

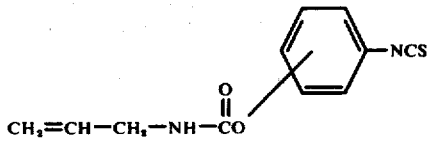

2. A compound according to claim 1 in which the isothiocyanate group is in the para position with respect to the carbamyloxy group.

3. A compound having the formula

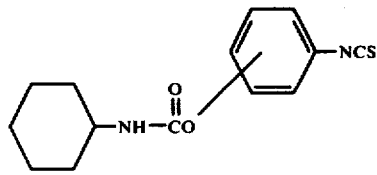

4. A compound according to claim 3 in which the isothiocyanate group is in the para position with respect to the carbamyloxy group.

5. A compound having the formula

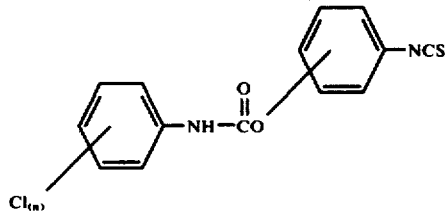

in which $n$ is 1 or 2.

6. A compound according to claim 5 in which $n$ is 1.

7. A compound according to claim 6 in which the $Cl_{(n)}$ group is o-chloro, and the isothiocyanate group is in the para position with respect to the carbamyloxy group.

8. A compound according to claim 6 in which the $Cl_{(n)}$ group is m-chloro and the isothiocyanate group is in the para position with respect to the carbamyloxy group.

9. A compound according to claim 6 in which the $Cl_{(n)}$ group is p-chloro and isothiocyanate group is in the para position with respect to the carbamyloxy group.

10. A compound according to claim 6 in which $n$ is 2.

11. A compound according to claim 10 in which the $Cl_{(n)}$ group is 3,4-dichloro and the isothiocyanate group is in the para position with respect to the carbamyloxy group.

12. A compound according to claim 10 in which the $Cl_{(n)}$ group is 3,4-dichloro and the isothiocyanate group is in the meta position with respect to the carbamyloxy group.

13. A compound having the formula

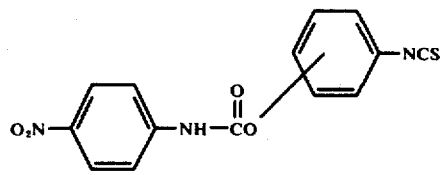

14. A compound according to claim 13 in which the isothiocyanate group is in the para position with respect to the carbamyloxy group.

15. A compound having the formula

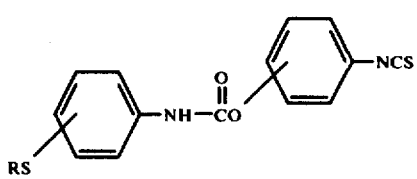

in which R is lower alkyl group having from 1 to 4 carbon atoms.

16. A compound according to claim 15 in which R is methyl, the thiomethyl group is in the para position on the phenyl ring and the isothiocyanate group is in the para position with respect to the carbamyloxy group.

17. A fungicidal composition of matter comprising a fungicidally effective amount of a compound having the formula

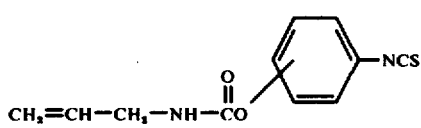

and an inert carrier.

18. A fungicidal composition of matter comprising a fungicidally effective amount of a compound having the formula

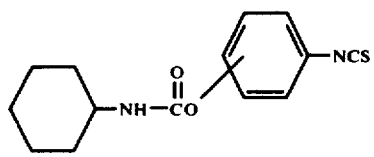

and an inert carrier.

19. A fungicidal composition of matter containing a fungicidally effective amount of a compound having the formula

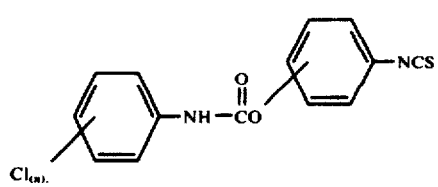

in which n is 1 or 2 and an inert carrier.

20. A fungicidal composition of matter comprising a fungicidally effective amount of a compound having the formula

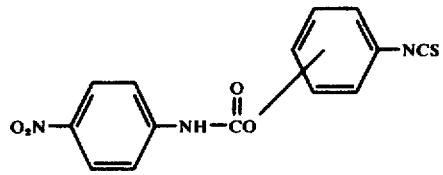

and an inert carrier.

21. A fungicidal composition of matter comprising a fungicidally effective amount of a compound having the formula

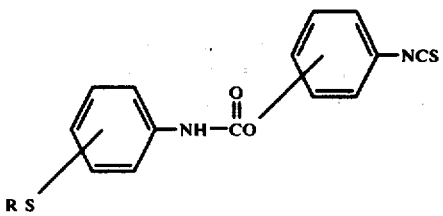

in which R is a lower alkyl group having from 1 to 4 carbon atoms, and an inert carrier.

22. A method of inhibiting the growth of fungi which comprises applying to the fungus or the locus thereof a fungicidally effective amount of a compound having the formula

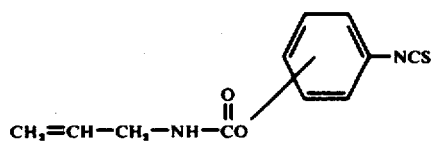

23. A method of inhibiting the growth of fungi which comprises applying to the fungus or the locus thereof a fungicidally effective amount of a compound having the formula

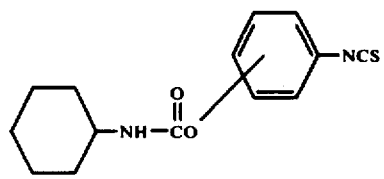

24. A method of inhibiting the growth of fungi which comprises applying to the fungus or the locus thereof a fungicidally effective amount of a compound having the formula

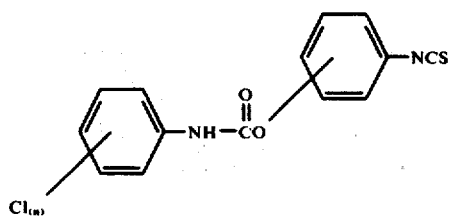

in which n is 1 or 2.

25. A method of inhibiting the growth of fungi which comprises applying to the fungus or the locus thereof a fungicidally effective amount of a compound having the formula

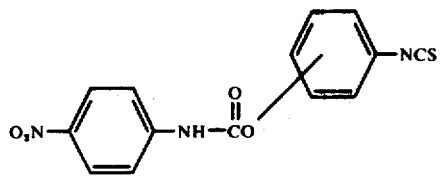

26. A method of inhibiting the growth of fungi which comprises applying to the fungus or the locus thereof a fungicidally effective amount of a compound having the formula

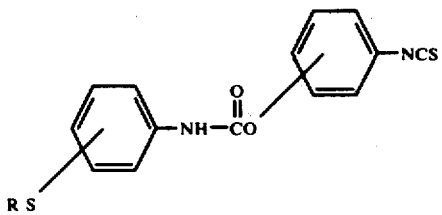

in which R is a lower alkyl group having from 1 to 4 carbon atoms.

* * * * *